(12) United States Patent
Law

(10) Patent No.: US 8,535,351 B1
(45) Date of Patent: Sep. 17, 2013

(54) DYNAMIC SPINAL STABILIZATION SYSTEM

(76) Inventor: Melvin Law, Brentwood, TN (US)

( * ) Notice: Subject to any disclaimer, the term of this patent is extended or adjusted under 35 U.S.C. 154(b) by 0 days.

(21) Appl. No.: 13/233,442

(22) Filed: Sep. 15, 2011

Related U.S. Application Data

(62) Division of application No. 12/480,085, filed on Jun. 8, 2009, now Pat. No. 8,043,340.

(51) Int. Cl.
*A61B 17/70* (2006.01)

(52) U.S. Cl.
USPC .................................................. 606/257

(58) Field of Classification Search
USPC ............................................ 606/246–279
See application file for complete search history.

(56) References Cited

U.S. PATENT DOCUMENTS

| | | | |
|---|---|---|---|
| 5,413,602 A | 5/1995 | Metz-Stavenhagen | |
| 5,672,175 A | 9/1997 | Martin | |
| 7,326,210 B2 | 2/2008 | Jahng et al. | |
| 7,699,875 B2 | 4/2010 | Timm | |
| 7,927,356 B2* | 4/2011 | Lim | 606/257 |
| 2002/0095154 A1 | 7/2002 | Atkinson et al. | |
| 2003/0220643 A1 | 11/2003 | Ferree | |
| 2004/0143264 A1 | 7/2004 | McAfee | |
| 2005/0143737 A1 | 6/2005 | Pafford et al. | |
| 2005/0177156 A1* | 8/2005 | Timm et al. | 606/61 |
| 2005/0203519 A1 | 9/2005 | Harms et al. | |
| 2006/0036240 A1 | 2/2006 | Colleran et al. | |
| 2006/0229613 A1* | 10/2006 | Timm et al. | 606/61 |
| 2006/0247635 A1 | 11/2006 | Gordon et al. | |
| 2006/0264937 A1 | 11/2006 | White | |
| 2006/0264940 A1 | 11/2006 | Hartman | |
| 2007/0233085 A1* | 10/2007 | Biedermann et al. | 606/61 |
| 2007/0288012 A1 | 12/2007 | Colleran et al. | |
| 2007/0293862 A1* | 12/2007 | Jackson | 606/61 |
| 2008/0140076 A1* | 6/2008 | Jackson | 606/60 |
| 2008/0147122 A1 | 6/2008 | Jackson | |
| 2008/0183213 A1* | 7/2008 | Veldman et al. | 606/257 |
| 2008/0195153 A1* | 8/2008 | Thompson | 606/257 |
| 2008/0300633 A1* | 12/2008 | Jackson | 606/257 |
| 2009/0093846 A1* | 4/2009 | Hestad | 606/255 |
| 2009/0099606 A1* | 4/2009 | Hestad et al. | 606/254 |
| 2009/0216274 A1* | 8/2009 | Morancy-Meister et al. | 606/247 |
| 2009/0259258 A1* | 10/2009 | Perez-Cruet et al. | 606/264 |
| 2009/0275985 A1* | 11/2009 | Jackson | 606/264 |
| 2009/0326584 A1 | 12/2009 | Slivka et al. | |
| 2010/0087862 A1 | 4/2010 | Biedermann et al. | |
| 2010/0087865 A1 | 4/2010 | Biedermann et al. | |
| 2010/0174319 A1 | 7/2010 | Jackson | |
| 2011/0029022 A1* | 2/2011 | Zehnder et al. | 606/264 |
| 2011/0082504 A1* | 4/2011 | Singhatat et al. | 606/249 |
| 2012/0035660 A1* | 2/2012 | Jackson | 606/257 |
| 2012/0041493 A1* | 2/2012 | Miller et al. | 606/264 |

* cited by examiner

*Primary Examiner* — Ellen C Hammond
*Assistant Examiner* — Stuart S Bray
(74) *Attorney, Agent, or Firm* — Luedeka Neely Group, PC

(57) ABSTRACT

A dynamic spinal stabilization system that enables spinal movements throughout a range of motions from a neutral condition of the spine, to a flexion condition, and an extension condition. The system includes metal pedicle screws and at least one metal support rod, wherein the system includes elastomeric members operatively located to substantially eliminate metal-to-metal contact of metal components of the system that are movable relative to one another.

5 Claims, 23 Drawing Sheets

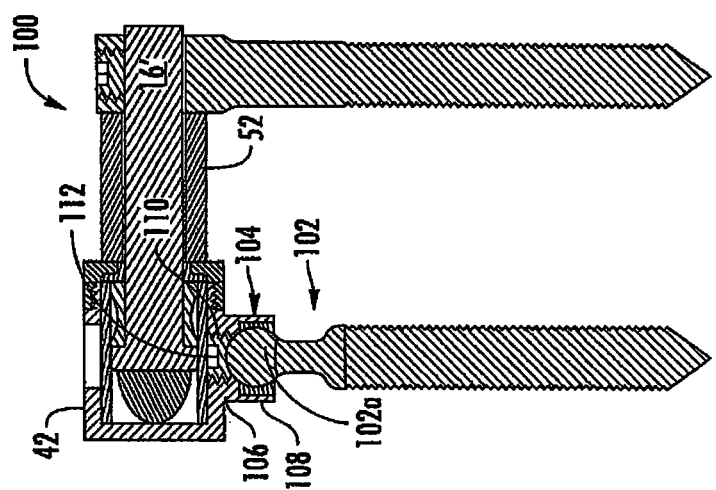
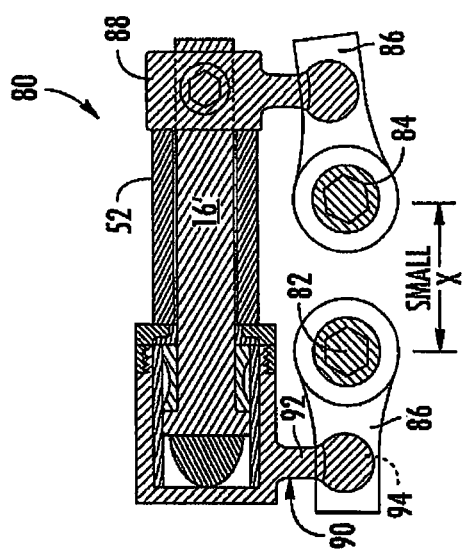
FIG. 5
FIG. 4

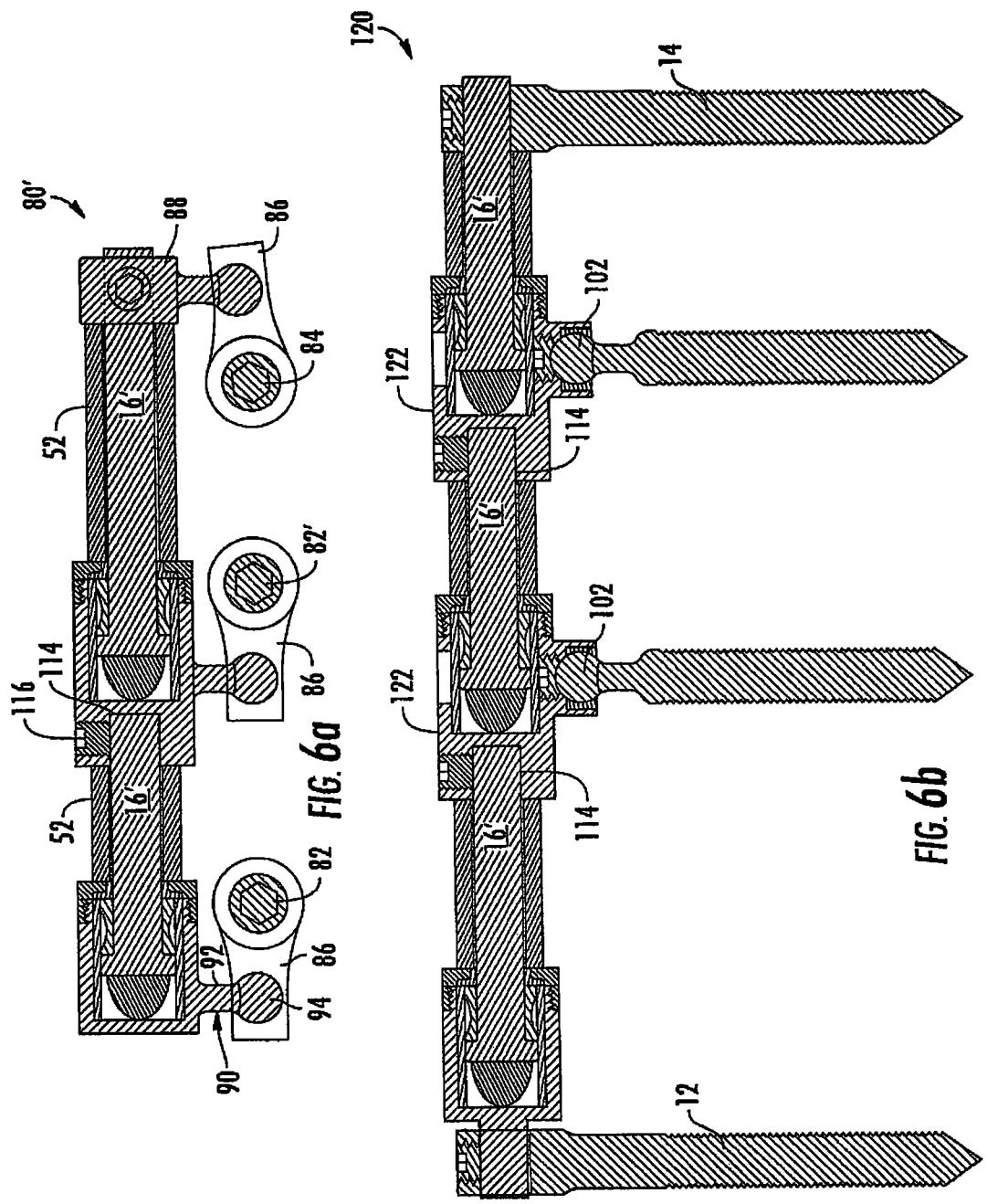

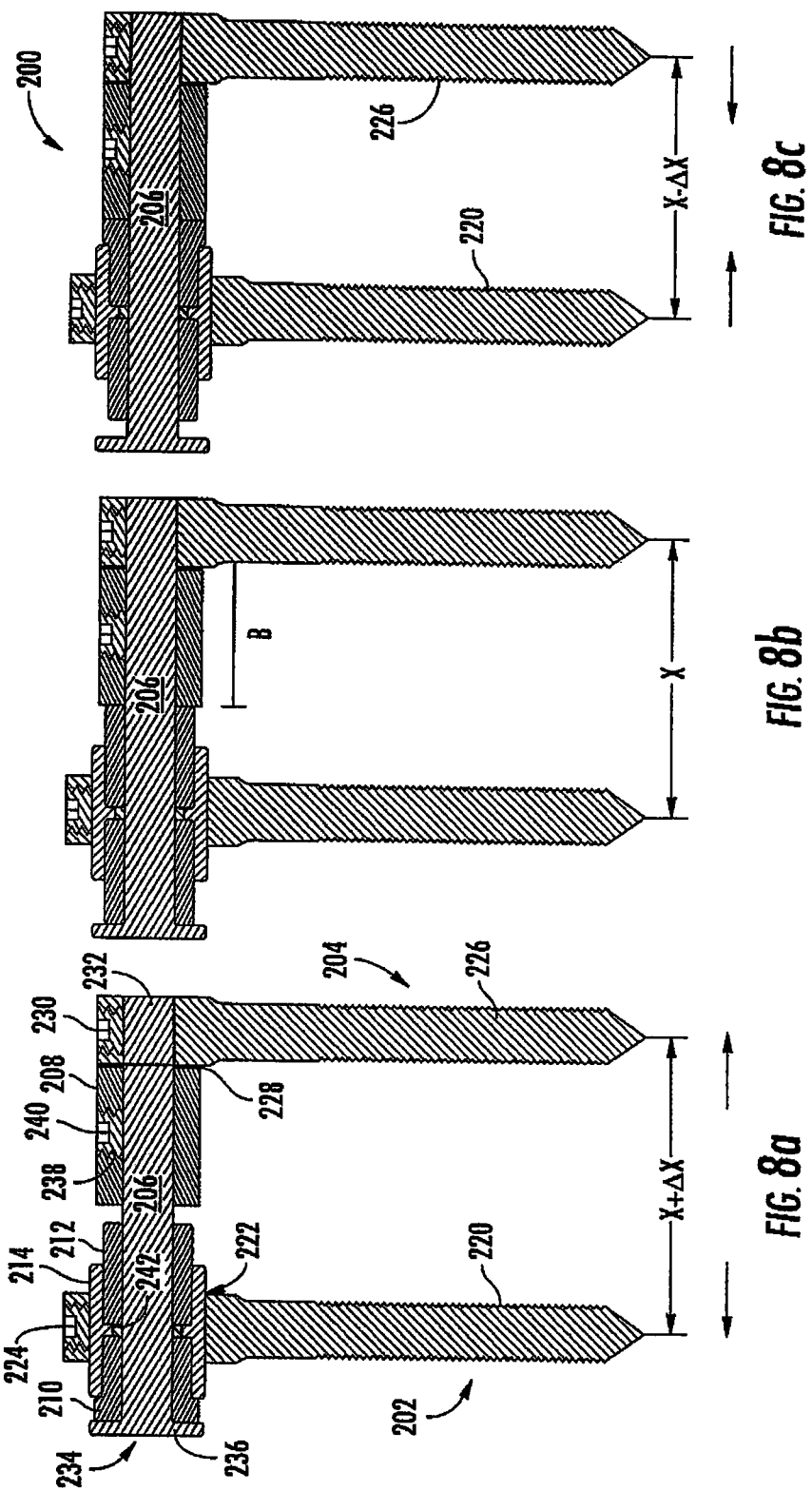

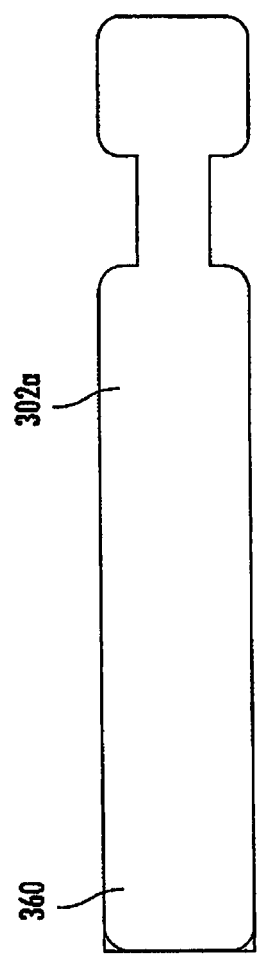
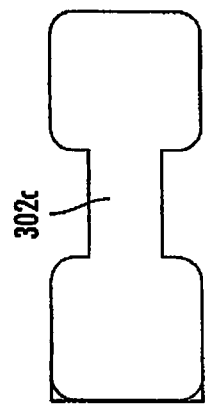
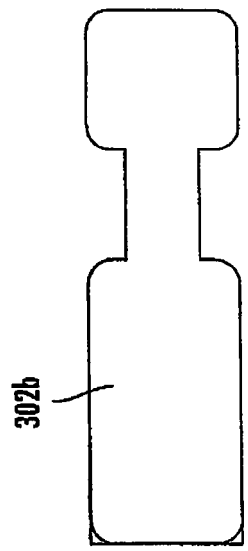
FIG. 19A
FIG. 19C
FIG. 19B

DYNAMIC SPINAL STABILIZATION SYSTEM

CROSS-REFERENCE TO RELATED APPLICATION

This is a divisional application of U.S. application Ser. No. 12/480,085, filed Jun. 8, 2009, and entitled DYNAMIC SPINAL STABILIZATION SYSTEM, now U.S. Pat. No. 8,043,340, which claims priority to U.S. Provisional Application Serial No. 61/059,899 filed Jun. 9, 2008, and entitled LUMBAR STABILIZER, each incorporated herein by reference in its entirety.

CROSS-REFERENCE TO RELATED APPLICATION

This application claims priority to U.S. Provisional Application Ser. No. 61/059,899 filed Jun. 9, 2008, and entitled "Spine Stabilizer," incorporated by reference herein in its entirety.

FIELD

This disclosure relates to the field of dynamic spinal stabilization devices. More particularly, this disclosure relates to dynamic spinal stabilization devices that utilize metal components, but which avoid metal-to-metal contact associated with relative movement of components.

BACKGROUND

While there are a variety of causes of spinal pain, in many instances such pain results from mis-alignment of members of the spine and/or changes in spacing of members of the spine. Often, these conditions result from degeneration, either from age or injury, of spinal discs. The primary surgical treatment options for disc degeneration are spinal fusion and dynamic stabilization.

Spinal fusion is a surgical procedure in which degenerated discs are removed and the resulting adjacent discs are held together by use of a rigid system of pedicle screws and rods until the discs grow together and fuse.

Dynamic stabilization is a surgical procedure that avoids disc removal and utilizes a flexible implant that restores desired alignment and spacing of vertebrae, relieves weight overload of individual discs, and permits substantially normal spinal movements. Improvement is desired in the provision of dynamic spinal stabilizers.

Spinal implants typically utilize various metal components, such as pedicle screws and rods. One problem associated with conventional dynamic stabilization devices is metal-to-metal contact of the various components, such as contact between the metal rod and the metal screw. Such metal-to-metal contact is undesirable, as metal-to-metal contact can result in metal flakes which flakes can be inflammatory and painful to the patient, and compromise the structural integrity of the stablizer.

Another disadvantage of conventional stabilizers is the presence of gaps between components of the stabilizer. Gaps are undesirable, as tissue can grow into gaps and interfere with the operation of the stabilizer and cause pain to the patient.

The present disclosure advantageously provides improved dynamic stabilization systems that avoid metal-to-metal contact of components that move relative to one another and minimize undesirable gaps between components of the system.

SUMMARY

The above and other needs are met by dynamic stabilization systems that enable spinal movements throughout a range of motions from a neutral condition of the spine, to a flexion condition, and an extension condition.

The systems include metal pedicle screws and at least one metal support rod, with elastomeric members operatively located to substantially eliminate metal-to-metal contact of metal components of the system that are movable relative to one another, and to minimize gaps between components of the system.

In one aspect, the stabilization system includes a first metal pedicle screw and a second metal pedicle screw each installable in a vertebrae; a metal support rod having a first end and an opposite second end having an enlarged diameter head; and a rod housing.

The rod housing includes a main body defining a bore having an open end configured to receive the head of the rod; a mount extending from an exterior surface of the main body, a cap secured adjacent the open end of the bore and including an aperture configured to permit passage of the rod therethrough, but not permit passage of the head of the rod therethrough, an elastomeric sleeve located exterior of the bore and adjacent and co-linear with the aperture of the cap, and one or more plastic inserts located interior the bore and configured to substantially surround portions of the rod within the main body and the cap. An elastomeric tip is located within the housing adjacent the head of the metal support rod.

The plastic inserts and the elastomeric tip are operative to substantially eliminate contact between the metal rod, the metal main body and the metal cap during movement of the rod relative to the main body and the cap so as to substantially eliminate metal-to-metal contact of metal components of the system that are movable relative to one another, with the system enabling spinal movements throughout a range of motions from a neutral condition of the spine, to a flexion condition, and an extension condition.

In another aspect, the disclosure provides a dynamic spinal stabilization system that includes a first metal pedicle screw and a second metal pedicle screw each installable in a vertebrae; a metal support rod having a first end having an enlarged diameter head and an opposite second end; a first metal spacer, first and second elastomeric sleeves, and a first sleeve mounting flange made of metal and having a circumferential raised rim located proximate the longitudinal midpoint of the flange.

The flange of the first sleeve mounting flange is secured within a head of the first pedicle screw, with the first and second elastomeric sleeves inserted within opposite ends of the first sleeve mounting flange so as to each about the circumferential rim thereof. The rod extends through the first and second sleeves and the first flange, so that the head of the rod is adjacent the first sleeve, with second end of the rod being rigidly connected to the second pedicle screw, and the first spacer rigidly affixed to the rod intermediate the second sleeve and the second pedicle screw.

In yet another aspect, the stabilization system includes a dumbbell shaped elastomeric member having a through bore configured to receive a metal support rod and including a central portion of reduced outer dimension, and a pair of opposite end portions having enlarged outer dimensions.

The system further includes a metal pedicle screw having a polyaxial head; a set screw threadably received by the polyaxial head; first and second rigid members securable to the rod; and a bottom partial sleeve positionable within a lower portion of the polyaxial head and a top partial sleeve positionable with an upper portion of the polyaxial head of the screw so as to mate with the bottom partial sleeve for receiving central portion of the dumbbell shaped elastomeric member.

When the sleeves are installed within the polyaxial head the sleeves capture the central portion of the dumbbell with the opposite end portions of the elastomeric member extending outwardly from opposite sides of the polyaxial head.

The dumbbell shaped elastomeric member is operative to substantially eliminate contact between the metal rod and the metal pedicle screw so as to substantially eliminate metal-to-metal contact of metal components of the system that are movable relative to one another, and the dumbbell shaped elastomeric deforms to enable movement of the rod relative to the pedicle screw so as to permit spinal movements throughout a range of motions from a neutral condition of the spine, to a flexion condition, and an extension condition.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIG. 4 shows an alternate embodiment of a system utilizing a polyaxial mount to attach a stabilizer to a pedicle screw.

FIG. 5 shows an alternate embodiment in which the system is configured for use with a polyaxial pedicle screw.

FIGS. 6A and 6B show a multi-level vertebrae stabilization system according to further embodiments of the disclosure.

FIGS. 8A-8C are cross-sectional views of an embodiment of a stabilization system that utilizes elastomeric sleeves and enables the head of the rod to move relative to the polyaxial head of a pedicle screw to which it is located.

FIGS. 19A-19C show alternate embodiments of the dumbbell shaped dampener of FIG. 14.

DETAILED DESCRIPTION

With reference to the drawings, the disclosure relates to dynamic stabilization systems that avoid metal-to-metal contact of components that move relative to one another and minimize undesirable gaps between components of the system. The systems described herein are particularly configured for use in stabilizing lumbar regions of the human spine, and are also suitable for use to stabilize the thoracic region.

Figures 1A, 1B, 1C:
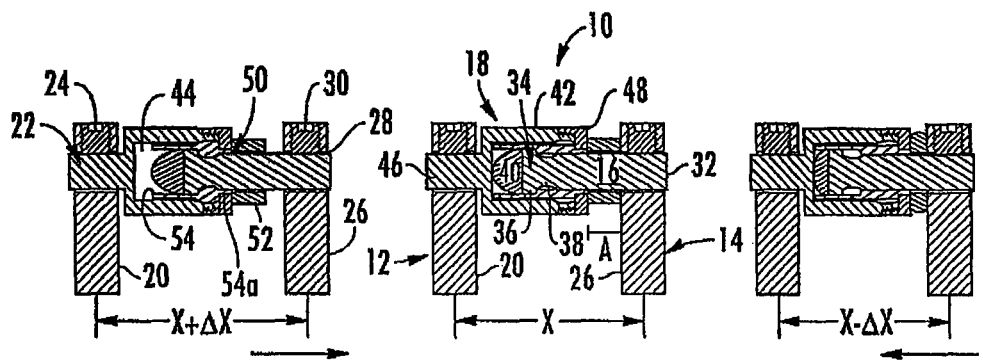
FIGS. 1A-1C are cross-sectional views of a dynamic stabilization system according to an embodiment of the disclosure, showing the stabilizer in conditions of flexion, neutral, and extension.

With reference to FIGS. 1A-1C, there is shown a dynamic stabilization system 10 having a pair of pedicle screws 12 and 14, a support rod 16, and a rod housing 18.

The pedicle screw 12 has a threaded shaft 20 configured to be screwed into bone and topped by a polyaxial head 22 that defines a threaded U-shaped channel configured to threadably receive a set screw 24. The screw 14 is identical to the screw 12 and includes a shaft 26, head 28, and set screw 30.

The support rod 16 is an elongate rod made of a biocompatible material suitable for implanting in the human body, such as biocompatible metals including titanium and alloys thereof, and of suitable dimensions for spinal stabilization purposes. The rod 16 is preferably of circular cross-section and has a planar first end 32 defined as by cutting the rod 16 perpendicular to its length, with the end 32 having the same diameter as the rod 16. An opposite second end 34 has an enlarged diameter head 36 and a reduced diameter neck 38 connecting the head 36 to the rod 16. That is, the head 36 has a diameter larger than the diameter of the rod 16, and the neck 38 has a diameter smaller than that of the rod 16. The rod 16 is preferably substantially straight, but, if desired may be bent or curved, such as to impart lordosis or inward curvature to the adjacent portion of the spine.

An elastomeric tip 40 is secured to the head 36 opposite the neck 38. The tip 40 is shown having a bullet or conical shape and may be made of biocompatible elastomeric materials such as silicone, polycarbonate urethane, and other biocompatible thermoplastic elastomers. The tip 40 is configured to yieldably bear against an interior portion of the rod housing 18, as explained below. Alternatively, the tip 40 may be secured to an interior portion of the rod housing 18 to bear against the head 36.

The rod housing 18 includes a main body 42 defining a blind bore 44 configured to receive the head 36 of the rod 16. A mount 46 extends from an exterior surface of the main body opposite the bore 44. The housing 18 further includes a cap 48 securable to the main body 42 adjacent the open end of the bore 44. The cap 48 may preferably be threadably received by the main body 42. The cap 48 includes an aperture 50 configured to permit passage of the rod 16 therethrough, but not permit passage of the head 36 of the rod 16 therethrough. This may be accomplished, for example, by providing the rod 16 with a diameter of other dimension of 6 mm, the aperture 50 with a diameter or other dimension of 6.1 mm, and the head 36 with a diameter or other dimension of 7 mm. The main body 42, the mount 46, and the cap 48 may each be made of a rigid biocompatible material, such as any material suitable for making the screws 12 and 14, and the rod 16.

An elastomeric sleeve 52 is secured to or adjacent to the exterior of the cap 48 so as to be co-linear with the aperture 50. The sleeve 52 may be made of the same materials as are suitable for the tip 40. The sleeve 52 preferably has an internal diameter or dimension corresponding to the diameter or dimension of the aperture 50. With reference to FIG. 1B, the sleeve 52 preferably has a length sufficient to substantially bridge a gap distance A defined between the cap 48 and the screw 14 when the system 10 is in a neutral environment corresponding to the spine on which the system 10 is installed, as explained more fully below.

A plastic insert 54 is located within the bore 44 of the main body 42, and also the aperture 50 of the cap 48, and configured to substantially surround the longitudinal dimension of the portions of the rod 16 within the main body 42 and the cap 48. The plastic insert 54 is preferably configured as a cylinder, having a terminal end 54a of reduced thickness to fit within the aperture 50 of the cap 48.

In this regard, the plastic insert 54 cooperates with the rod 16 and the main body 42 and the cap 48 to substantially eliminate any contact between the rod 16, which may be of metal, and the main body 42 and the cap 48, which may be of metal, during movement of the rod 16 relative to the main body 42 and the cap 48. The plastic insert 54 also serves to frictionally engage the rod 16 to provide a desired resistance to travel of the rod 16 so that the rod is yiedably positionable and travels in a controlled manner relative to the force applied by spinal movements. In addition, the plastic insert 54 is further configured to cooperate with the head 36 and the neck 38 to restrain the head 36 from passage through the cap 48, as best seen in FIG. 1A, which shows the portion of the insert 54 adjacent the neck 38 deforming into and filling the neck 38 and the portion of the bore 44 adjacent the neck 38 when the end 36 of the rod 16 is urged toward the cap 48, such as during flexion of the spine. Preferred biocompatible materials for the insert 54 include polycarbonate urethanes.

As will be appreciated, the rod 16 and the portions thereof are described in dimensional terms corresponding to a rod having a circular cross-section. However, it will be understood that the rod and portions thereof, and the other components of the system that cooperate therewith, may be otherwise configured, such as polygonal cross-sections, oval, and the like.

The rod 16 and rod housing 18 may be assembled together by positioning the plastic insert 54 within the bore 44 and then sliding the head 36 into the bore 44 so that the tip 40 is adjacent the blind end of the bore 44. Next, the aperture 50 of the cap 48 and the sleeve 52, which is secured to the cap 48, are placed over the end 32 of the rod 16 and the cap 48 is secured to the main body 42. The thus assembled rod 16 and housing 18 are then installed onto the screws 12 and 14, which are installed within the patient, to provide the system 10. This may be accomplished by securing the mount 46 within the head 22 of the screw 12 using the set screw 24, and securing the end 32 of the rod 16 within the head 28 of the screw 14 using the set screw 30.

The system 10 is initially installed into a patient with the spine in a neutral condition, as opposed to conditions of flexion or extension. Neutral spine is the natural position of the spine, characterized by the presence of curves in the thoracic (upper) and lumbar (lower) regions. That is, there is presented a slight forward curve in the lumbar region (lordosis), a slight backward curve in the thoracic region (kyphosis) and a slight extension of cervical vertebra at the top of the spinecervical (neck). Flexion of the spine relates to conditions of the spine during forward bending, while extension of the spine relates to conditions of the spine during backward bending.

With additional reference to FIGS. 1A-1C, the system 10 is shown enabling improvement in spinal movements throughout the substantially normal range of motions from the neutral condition (FIG. 1B), to a flexion condition (FIG. 1A) and an extension condition (FIG. 1C). As shown in FIG. 1B, the screws 12 and 14 are initially a distance X apart. This corresponds to the spine onto which the system 10 is installed being in the neutral condition, with the screws 12 and 14 installed in adjacent vertebrae of the spine. As will be observed, the sleeve 52 substantially occupies the gap A. In this regard, when the spine is at rest, it will typically be in the neutral conditions. Thus, it is desirable to substantially fill the gap A with the sleeve 52 for the neutral condition of the spine. That is, while it will be seen that some gap remains between the sleeve 52 and the screw 14 during flexion, such gap is very minimal and generally the spine will be in transition and not statically maintained in flexion. During extension, the sleeve 52 occupies the entirety of the gap.

In addition, it will be observed that metal-to-metal contact between metal components that are movable relative to one another is eliminated by the system 10. That is, the rod 16, the main body 42, and the cap 48 may preferably be made of metal and are movable relative to one another, and the rod 16 has relative movement between the main body 42 and the cap 48, as is apparent from comparison of the relative positioning of the screws and the rod in FIGS. 1A-1C.

For example, in the event the screws 12 and 14 move apart a distance $\Delta x$, such as occurs during flexion of the spine (FIG. 1A), the plastic insert 54 is positioned between the rod 16 and any adjacent portions of the main body 42 and the cap 48, which represent potential metal-to-metal contact sites during a transition from neutral to flexion conditions of the spine. The plastic insert 54 serves in this same capacity when a transition to extension conditions of the spine are experienced, in which case the screws are located closer to one another by the distance $\Delta x$, for example.

In addition, during extension the tip 40 further acts to prevent any metal-to-metal contact between the end 36 of the rod 16 and the blind end of the bore 44, and the sleeve 52 prevents metal-to-metal contact between the cap 48 and the screw 14 during extension as seen in FIG. 1C. It will be appreciated that the tip 40 may alternatively be secured to the blind end of the bore 44 for contacting the end 36 of the rod 16. The deformations of the tip 40, sleeve 52 and insert 54 through the various ranges of motion of the spine, such as during extension and flexion, enable controlled absorbance of forces exerted by the rod in compression of the tip 40, sleeve 52, and insert 54, and thereby control movement of the rod in a desired manner to enable desired dynamic stabilization of the spine.

Thus, as will be appreciated, the system 10 advantageously provides a dynamic stabilization system that avoids metal-to-metal contact of components that move relative to one another and minimizes undesirable gaps between components of the system.

Figures 2A, 2B, 2C:
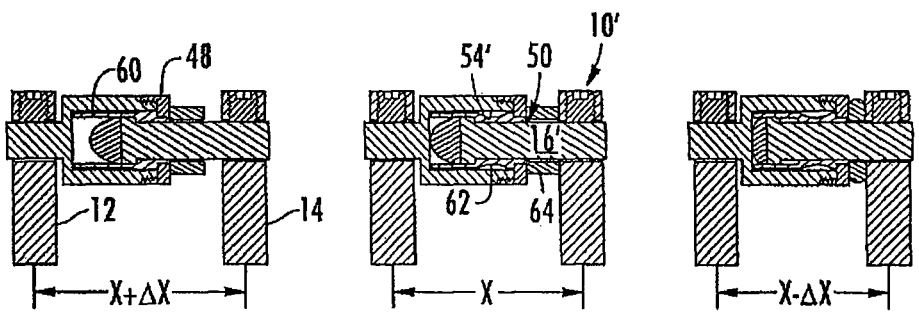
FIGS. 2A-2C are cross-sectional views of a dynamic stabilization system according an alternate embodiment of the disclosure, showing the system in conditions of flexion, neutral, and extension.

With reference now to FIGS. 2A-2C, there is shown an alternate embodiment of a dynamic stabilization system 10'. The system 10 is substantially identical to the system 10, except that the system 10' includes a rod 16' and a plastic insert 54', instead of the rod 16 and plastic insert 54. In this regard, the rod 16' is substantially identical to the rod 16, except that the rod 16' does not include any structure corresponding to the neck 38 of the rod 16. That is, the rod 16' includes the head 36 without having the neck 38. Accordingly, the plastic insert 54' is configured to cooperate with the head 36 of the rod 16' to restrain the head 36 from passage through the cap 48, as best seen in FIG. 2A, when the end 36 of the rod 16' is urged toward the cap 48, such as during flexion of the spine. The characteristics of the insert 54' also enable desired control over the movement of the rod 16'.

To provide such cooperation with the head 36 of the rod 16, the plastic insert 54' is preferably configured as a cylinder, with a reduced thickness portion 60 of the cylinder remote from the cap 48 and extending from the head 36 to the end of the blind bore 44 when the insert 54' is in an unflexed or uncompressed orientation, such as seen in FIG. 1*b*. A thicker scalloped or bowed region 62 of the insert 54' is included between the portion 60 and a terminal end 64 of reduced thickness to fit within the aperture 50 of the cap 48. Returning to FIG. 2A, the scalloped region 62 deforms into and fills the portion of the bore 44 between the head 36 and the cap 48 when the end 36 of the rod 16 is urged toward the cap 48, such as during flexion of the spine.

Figures 3A, 3B:
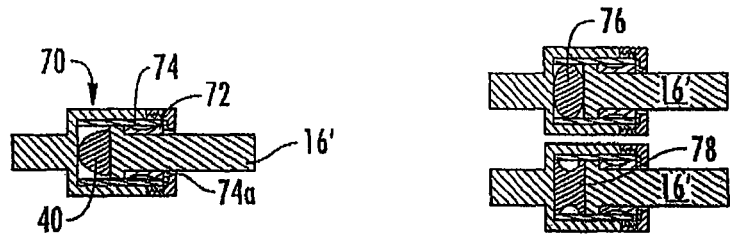
FIGS. 3A and 3B show additional embodiments of stabilization systems according to the disclosure.

With reference now to FIG. 3A, there is shown an alternate embodiment of a rod housing 70 that utilizes the rod 16'. However, instead of using a one-piece plastic insert, such as the insert 54', two inserts 72 and 74 are utilized. For example, the insert 72 is configured to function in the manner of the scalloped region 62 of the insert 54' and is shaped similar to the scalloped region 62, except it is provided alone to lie between the head 36 and the cap 48 and serve to deform into and fill the portion of the bore 44 between the head 36 and the cap 48 when the end 36 of the rod 16 is urged toward the cap 48, such as during flexion of the spine, and thereby control movement of the rod 16 in a desired manner. The insert 74 is configured as a cylinder and located between the rod 16' and the main body 42 and the cap 48 to substantially eliminate any contact therebetween during relative movement of the rod 16.' To accommodate the smaller diameter of the aperture 50 of the cap 48, a terminal end 74*a* of the inert 74 is of reduced diameter. If desired, the insert 74 may be of two-piece construction, with the terminal end 74*a* being a separate piece.

An advantage of the use of the separate inserts 72 and 74, or three if the end 74*a* is separate, is that different materials may be readily utilized. For example, it may be desirable that the insert 72 be softer or more deformable than the insert 74, due to the additional function of the insert 72 in deforming as the head 36 approaches the cap 48.

With reference to FIG. 3B, there is shown alternate configurations for the elastomeric tip 40, with an egg-shaped tip 76 and an I-shaped tip 78 being substituted for the bullet-shaped tip 40. The different shapes and/or materials for such tips will enable various deformation characteristics to enable desired dynamic stabilization of the spine.

Turning now to FIG. 4, there is shown an alternate embodiment of a dynamic stabilization system 80. The system 80 utilizes standard head pedicle screws 82 and 84, instead of the screws 12 and 14 having polyaxial heads. A standard omni-axial connector 86 is secured to each of the screws 82 and 84. A ball-connector 88 is utilized to connect the rod 16' to the connector 86 and, hence, the screw 14. However, to enable the rod housing to be connected to the connector 86 associated with the screw 12, a housing mount 90 is utilized. The mount 90 may be used with a housing corresponding to the various housings described herein, such as the rod housing 18 and the rod housing 70. The mount 90 is provided by an extension 92 extending from a side of the housing, terminating in a ball 94. The system 80 is particularly suitable for use when the pedicle screws are closely spaced.

With reference to FIG. 5, there is shown a still further embodiment of a dynamic stabilization system 100. The system 100 uses the screw 14, described previously, and a ball-headed pedicle screw 102. To enable the rod housing to be connected to the screw, a ball mount 104 is utilized. The mount 104 may be used with a housing corresponding to the various housings described herein, such as the rod housing 18 and the rod housing 70. The mount 104 is provided by an extension 106 that extends from a bottom surface of the main body 42 of the rod housing and has a lower end 108 configured to engage a ball 102*a* of the screw 102. A threaded bore 110 is located between the bore 44 of the housing and extension 106 for insertion of a set screw 112. Thus, during installation of the system 100, the housing must be connected to the screw 102 using the set screw 112 prior to assembly of the housing by installation of the rod, cap and plastic inserts. The system 100 is particularly suitable for installation sites wherein the orientation of the housing relative to the longitudinal axis of the screw 102 must be adjusted.

Turning now to FIG. 6A, there is shown a multi-level system 80' which provides a modification of the system 80 by inclusion of an additional standard head pedicle screw 82'. As will be appreciated, the rod housing associated with the pedicle screw 82' is modified to include a receiver 114 and cooperating set screw 116 for installation of the end of a rod, such as an end of an adjacent one of the rods 16'. The receiver 114 may be used with a housing corresponding to the various housings described herein, such as the rod housing 18 and the rod housing 70.

FIG. 6B shows another embodiment of a multilevel system 120, which combines various aspects of the previously described systems to utilize a combination of ball-headed pedicle screws 102 and screws having a polyaxial head, such as screws 12 and 14. For example, rod housings 122 associated with ball-headed screws 102 include the receiver 114 and the ball mount 104 described previously.

Figure 7A:
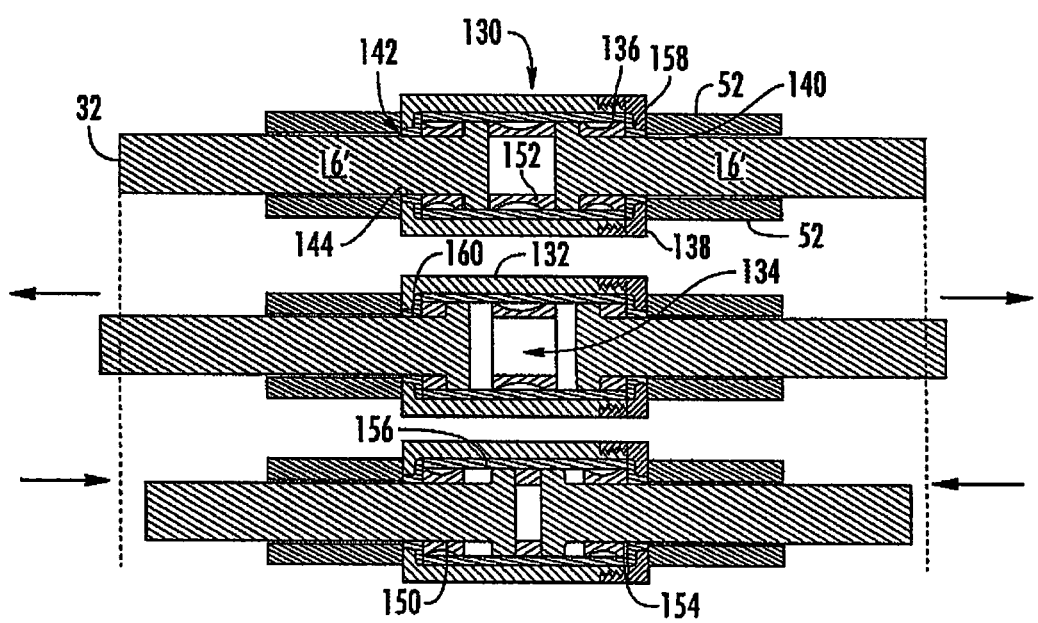
FIGS. 7A-7C show a further embodiment of a dynamic stabilization system that enables movement of adjacent rods aligned head-to-head.
Figure 7B:
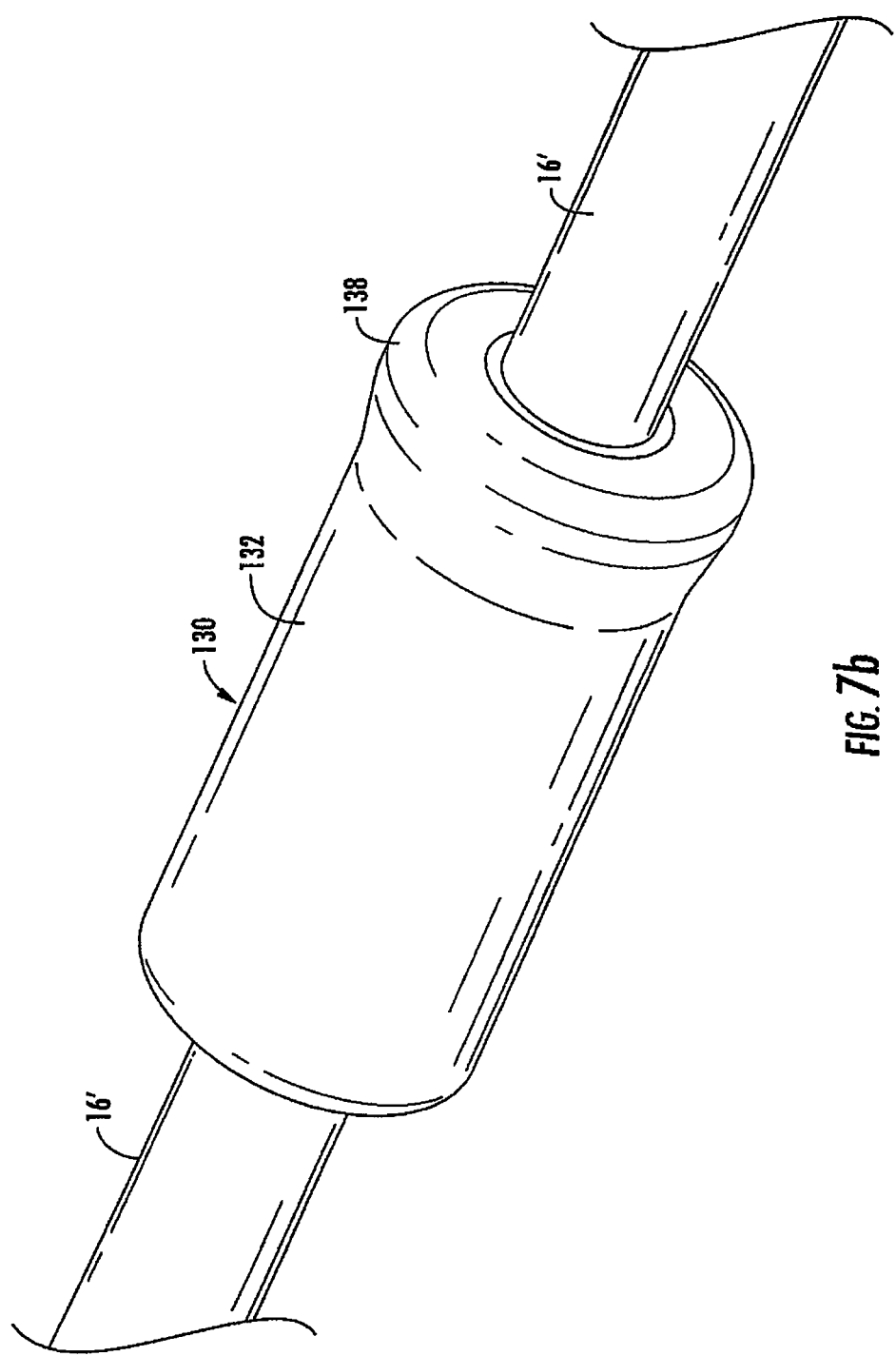
Figure 7C:
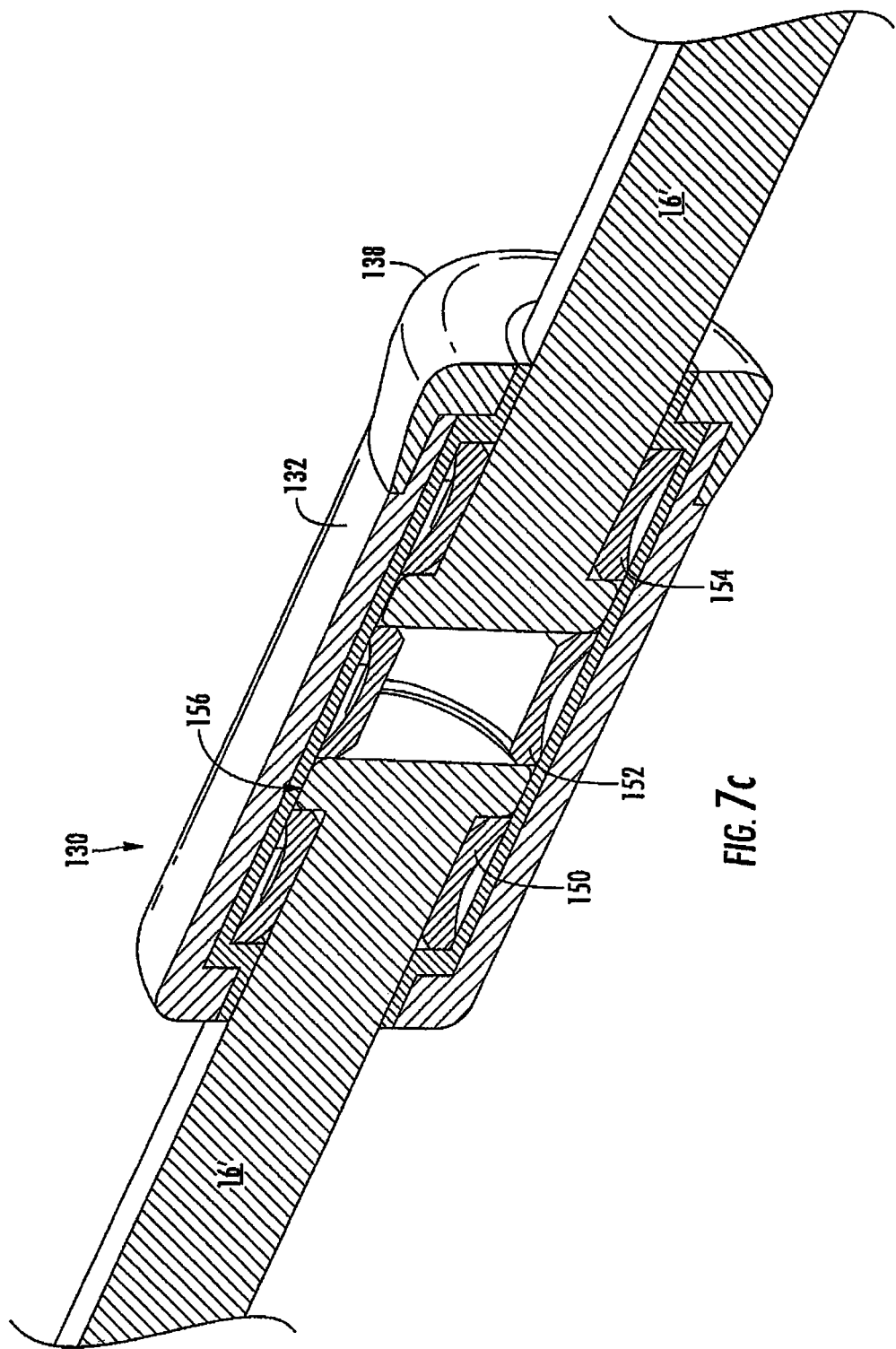

Turning now to FIGS. 7A-7C, there is shown a rod housing 130 configured for receiving a pair of the rods 16' and to permit desired controlled movement of each of the rods 16' relative to the rod housing 130. FIG. 7A shows, from top down, the housing when the spine is in a neutral condition, under conditions of flexion, and under conditions of extension. Each first end 32 of the rods 16' that extend outwardly of the housing 130 may be connected to a pedicle screw in the manners previously described for connecting the first ends 32 of the rods 16 and 16' in the various embodiments. In a similar manner, it will be understood that the housing 130 may alternatively be configured for receiving one or more of the rods 16, with utilization of the plastic inserts configured for use with rods 16.

The rod housing 130 includes a main body 132 defining a through bore 134 configured to receive the heads 36 of each of the rods 16', with the heads 36 adjacent one another. A first end 136 of the housing 130 is open and includes a cap 138 securable to the first end 136. The cap 138 preferably corresponds to the cap 48 and may be threadably received by the first end 136. The cap 138 includes an aperture 140 configured in the manner of the aperture 50 of the cap 48, and configured to permit passage of the rod 16' therethrough, but not permit passage, of the head 36 of the rod 16' therethrough. A second end 142 of the body 132 includes an aperture 144, which is configured similar to the aperture 140 and configured to permit passage of the rod 16' therethrough, but not permit passage of the head 36 of the rod 16' therethrough.

To prevent metal-to-metal contact, a plurality of plastic inserts 150, 152, 154, and 156 are included in the bore 134. The inserts 150, 152, and 154 preferably correspond to the insert 72 described in connection with FIG. 3A. The insert 156 preferably corresponds to the insert 74, but configured to fit the bore 134 and the apertures 140 and 144. In addition, one of the sleeves 52 is preferably positioned on the rods 16' exterior of the main body 132 in the manner previously described for the sleeve 52.

As may be seen by the depictions in FIG. 7A, which shows movement of the rods 16' relative to the housing 130, the housing 130 with the inserts thereof advantageously enables the reduction, if not elimination of metal-to-metal contact of moving parts and also supplies desired resistance to travel of the rods 16' so that the rods travel in a controlled manner relative to the force applied by spinal movements to enable desired dynamic stabilization of the spine.

With reference now to FIGS. 8A-8C, there is shown a dynamic stabilization system 200 having a pair of pedicle screws 202 and 204, a support rod 206, a rigid spacer 208, a pair of elastomeric sleeves 210, 212, and a sleeve mounting flange 214.

The pedicle screw 202 pedicle screw has a threaded shaft 220 configured to be screwed into bone and topped by a polyaxial head 222 that defines a threaded U-shaped channel configured to threadably receive a set screw 224. The screw 204 is identical to the screw 202 and includes a shaft 226, head 228, and set screw 230.

The support rod 206 is an elongate rod made of a biocompatible material suitable for implanting in the human body, such as biocompatible metals including titanium and alloys thereof, and of suitable dimensions for spinal stabilization purposes. The rod 206 is preferably of circular cross-section and has a planar first end 232 defined as by cutting the rod 206 perpendicular to its length, with the end 232 having the same diameter as the rod 206. An opposite second end 234 has an enlarged diameter head 236.

The rigid spacer 208 is preferably a cylindrical sleeve having threaded bore 238 for receiving a set screw 240. The spacer 208 and set screw 240 are preferably made of biocompatible metal materials.

The elastomeric sleeves 210 and 212 are preferably identical to one another and have a generally cylindrical shape and are made of a biocompatible elastomeric material.

The sleeve mounting flange 214 is preferably a cylinder having an interior circumferential raised rim 242 located proximate the longitudinal midpoint of the flange 214. The flange 214 is preferably of one-piece construction and made of a biocompatible metal material.

In assembly of the system 200, the elastomeric sleeves 210 and 212 are installed using the flange 214 which is secured within the head 222 of the pedicle screw 202 by the set screw 204. The rod 206 is passed through the sleeves 210 and 212, and the flange 214, so that the head 236 of the rod 206 is adjacent the sleeve 210. The end 232 of the rod 206 is rigidly connected to the screw 204 using the set screw 230 and the spacer 208 rigidly affixed by the set screw 240 to the rod 206 adjacent the end 232 of the rod 206. The spacer 208 advantageously has a length sufficient to substantially bridge a gap distance B defined between the screw 204 and the sleeve 212 when the system 200 is in a neutral environment corresponding to the spine on which the system 10 is installed.

The elastomeric sleeves 210 and 212 function to compress during flexion and extension events, which enables the head 236 of the rod 206 to move longitudinally relative to the pedicle screw 202 in a desired controlled manner. For example, in FIGS. 8A-8C, the system 200 is shown enabling improvement in spinal movements throughout the substantially normal range of motions from the neutral condition (FIG. 8B), to a flexion condition (FIG. 8A) and an extension condition (FIG. 8C).

As shown in FIG. 8B, the screws 202 and 204 are initially a distance X apart. This corresponds to the spine onto which the system 200 is installed being in the neutral condition, with the screws 202 and 204 installed in adjacent vertebrae. As will be observed, the spacer 208 and the sleeve 212 substantially occupy the gap B. In this regard, when the spine is at rest, it will typically be in the neutral condition. Thus, it is desirable to substantially fill the gap B with the sleeve 212 and the spacer 208 for the neutral condition of the spine. That is, while it will be seen in FIG. 8A that some gap remains between during flexion, such gap is very minimal and generally the spine will be in transition and not statically maintained in flexion. During extension, the sleeve 212 is compressed and the sleeve 212 and the spacer 208 occupy the entirety of the gap B.

In addition, it will be observed that metal-to-metal contact between metal components that are movable relative to one another is eliminated by the system 200. That is, the rod 206, the screw 202, and the metal flange 214 are each preferably made of metal, and the rod 206 has movement relative to the screw 202 and the flange 214; as is apparent from comparison of the relative positioning of the screws and the rod in FIGS. 8A-8C.

For example, in the event the screws 202 and 204 move apart a distance Δx, such as occurs during flexion of the spine (FIG. 8A), the sleeves 210 and 212 prevent any metal-to-metal contact sites during a transition from neutral to flexion conditions of the spine, or during a transition to extension conditions of the spine when the screws become located closer to one another by the distance Δx. In addition, during extension the sleeve 212 further acts to prevent any metal-to-metal contact between the flange 214 and the metal spacer 208, as seen in FIG. 8C. It will further be understood that the elastomeric and deformable components also function to control rod movement in a desired manner to enable desired dynamic stabilization of the spine.

Thus, as will be appreciated, the system 200 advantageously provides a dynamic stabilization system that avoids metal-to-metal contact of components that move relative to one another and minimizes undesirable gaps between components of the system.

Figure 9:
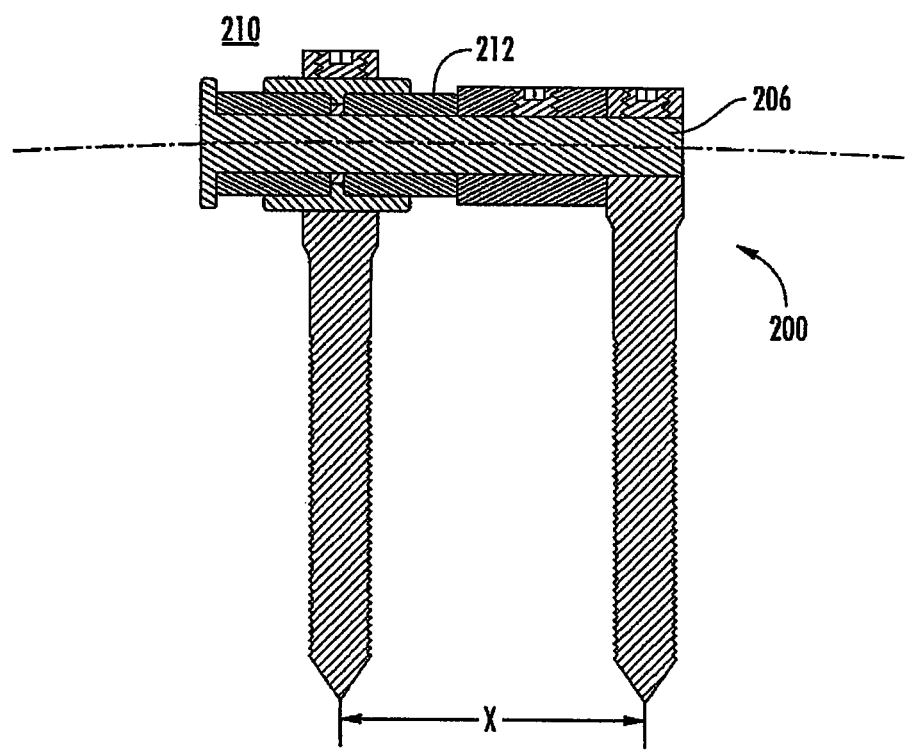
FIG. 9 shows additional movement of the system of FIGS. 8A-8C enabled by the use of elastomeric sleeves.

With additional reference to FIG. 9, the sleeves 210 and 212 also enable some other small movement of the rod 206 in other directions. For example, if spinal forces elevate the distal end of the rod 202, then the sleeves 210 and 212 enable some canting of the rod 206 by compressing.

Figure 10:
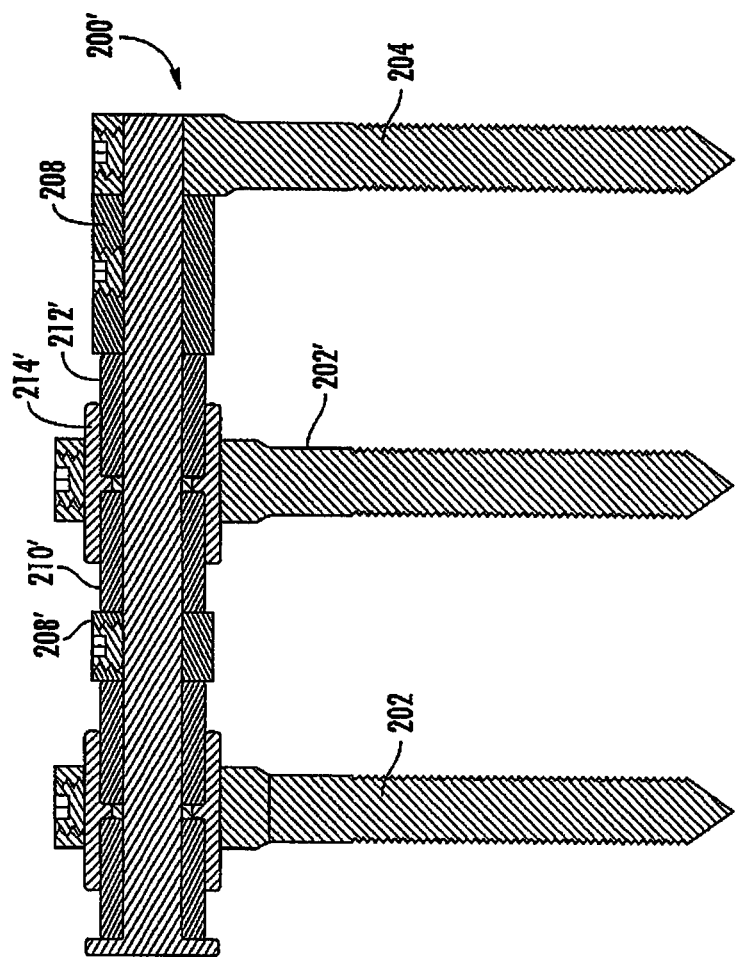
FIG. 10 is a cross-sectional view of a two-level stabilization system utilizing elastomeric sleeves.
Figure 11A:
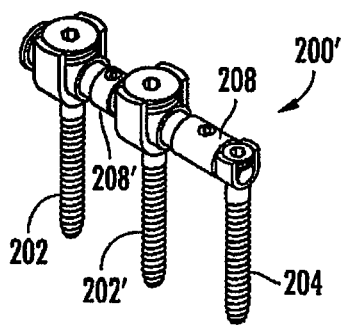
FIG. 11A is a perspective view of the system of FIG. 10.
Figure 11B:
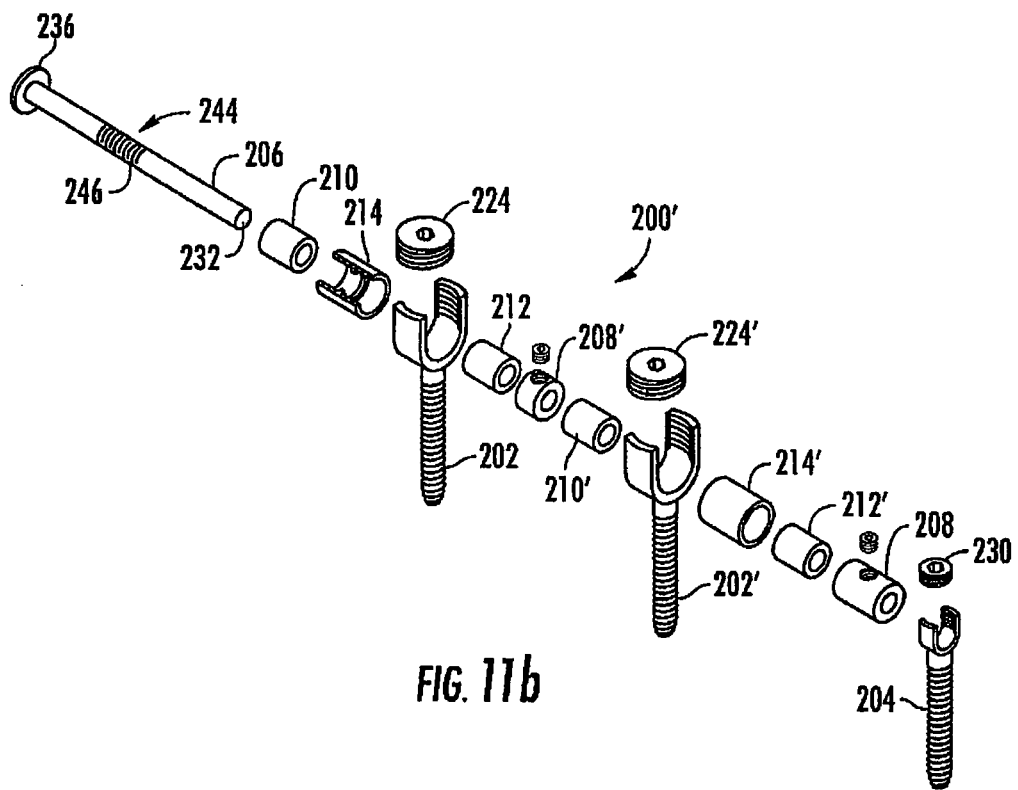
FIG. 11B is an exploded perspective view.

In an alternate system 200', additional pedicle screws, such as a pedicle screw 202' including set screw 224', and having elastomeric sleeves 210' and 212', and sleeve mounting flange 214' installed in the head, and additional rigid spacers, such as spacer 208', may be utilized, such as shown in FIGS. 10 and 11A-11B. As also seen in FIG. 11B, a rod 206' is utilized which includes a mid-portion 244 thereof made of a substantially yieldable material, such as a spring 246. The rod 206' may advantageously be utilized if increased bending of the system is desired.

Figure 12:
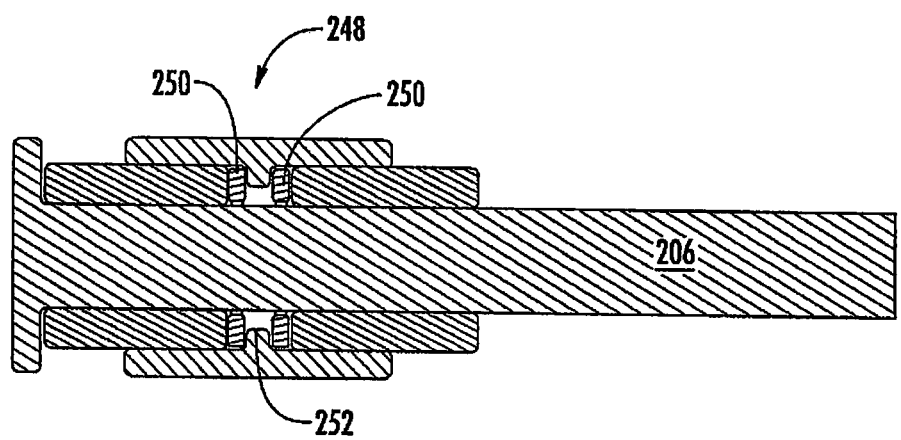
FIG. 12 shows an alternate embodiment of the system of FIGS. 8A-8C, which utilizes washers in connection with the elastomeric sleeves.

FIG. 12 shows an alternate embodiment of the system of FIGS. 8A-8C, which utilizes a flange 248 having plastic washers 250, preferably made of a medical grade polyethylene, carbon fiber, or polyetheretherketone, in connection with the elastomeric sleeves 210 and 210. The use of the washers 250 enables the use of a rim 252 on the flange 248 that is shorter than the rim 242 of the flange 214. This is advantageous to further protect against metal-to-metal contact between the rim of the flange and the rod, especially if the rod 206' is utilized.

With reference to FIGS. 13A-13C, 14, 15, 16A, and 16B, there is shown a further embodiment of a dynamic stabilization system 300 that utilizes a dumbbell shaped elastomeric member 302 that functions as a dampener, as will be explained more fully below. A support rod 304 passes through the elastomeric member 302. The elastomeric member 302 having the rod 304 therethough is received by a pedicle screw 306 and bounded by rigid members 308 and 310 secured in place by set screws 308a and 310a, respectively.

Figure 13A:
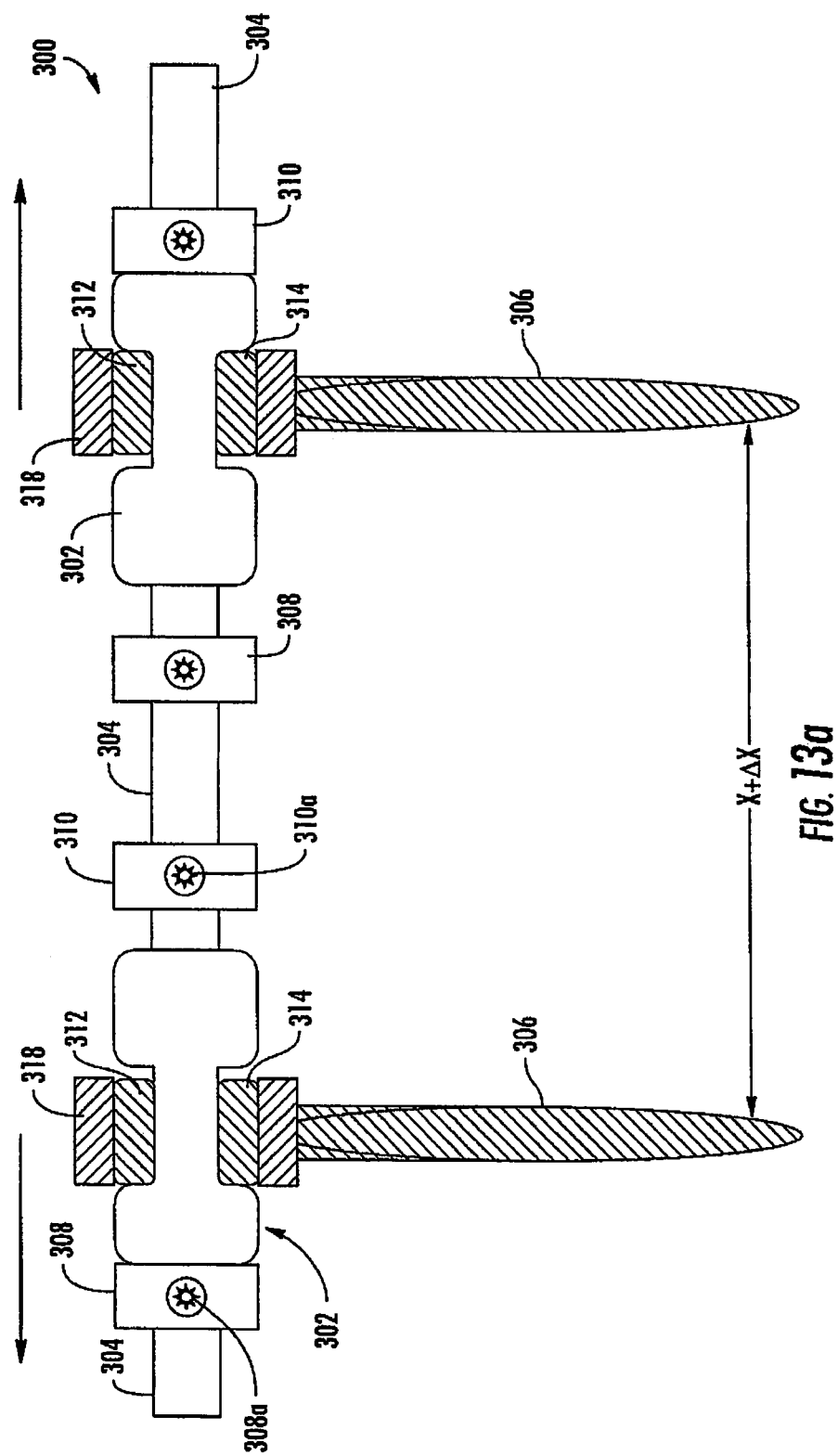
FIGS. 13A-13C show a further embodiment of a dynamic stabilization system that utilizes a dumbbell shaped dampener.
Figure 13B:
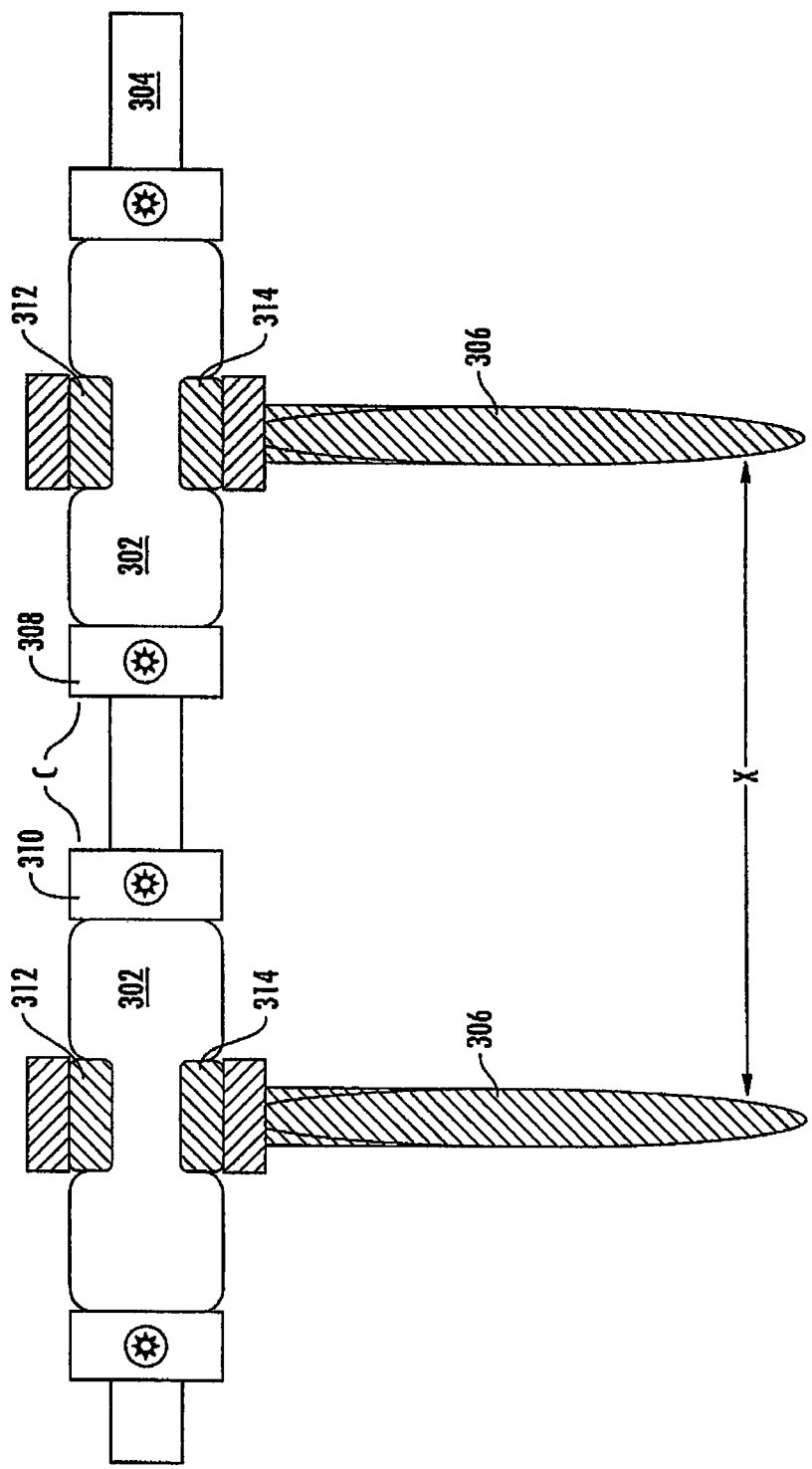
Figure 13C:
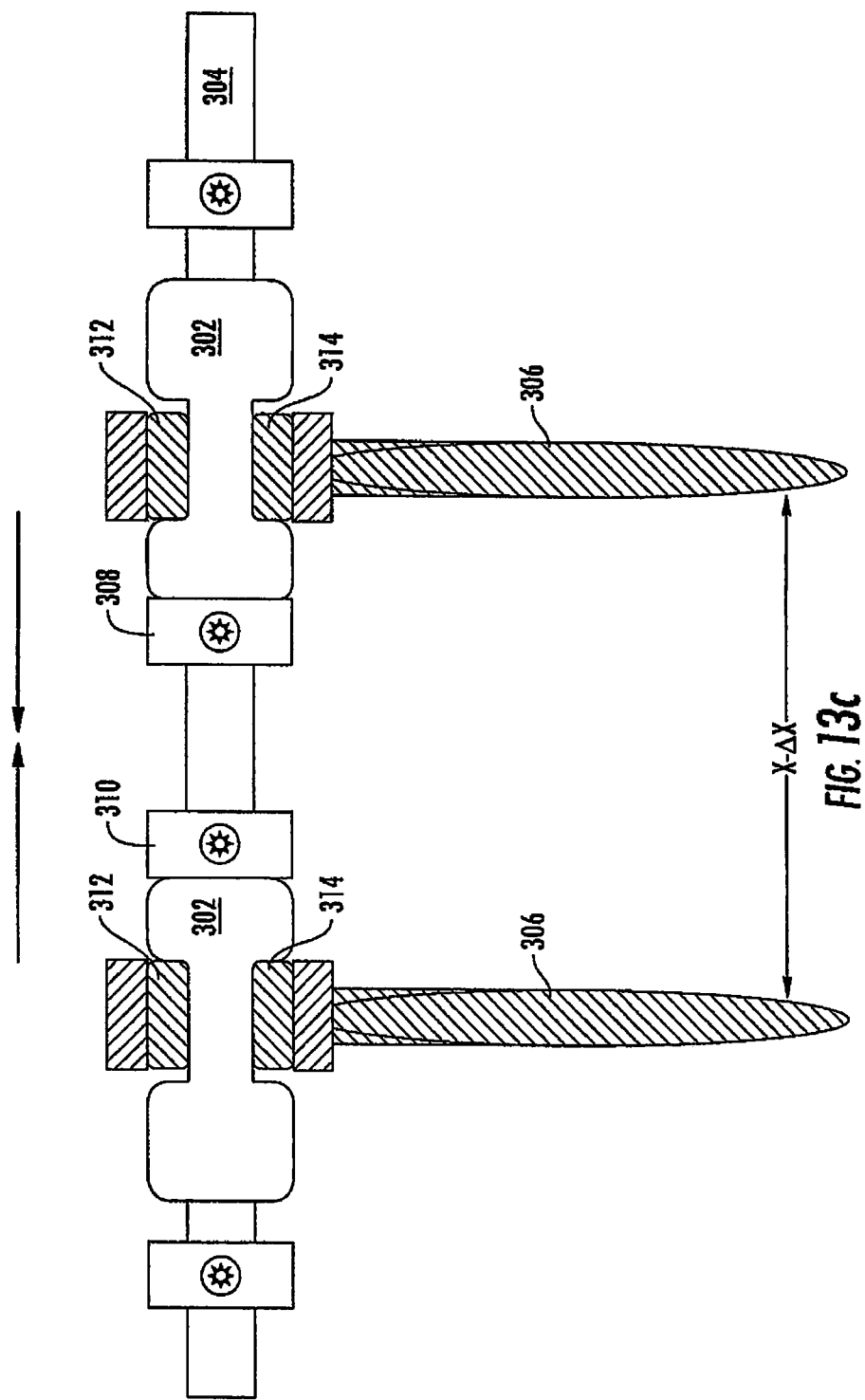
Figure 16A:
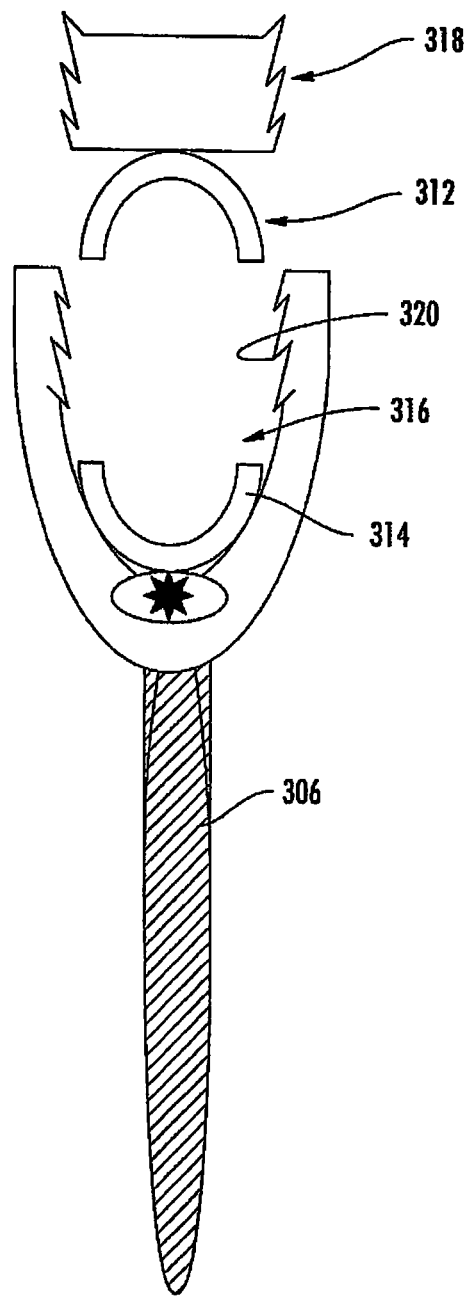
FIGS. 16A and 16B are cross-sectional views showing pedicle screw and ring components of the system of FIGS. 13A-13C.
Figure 16B:
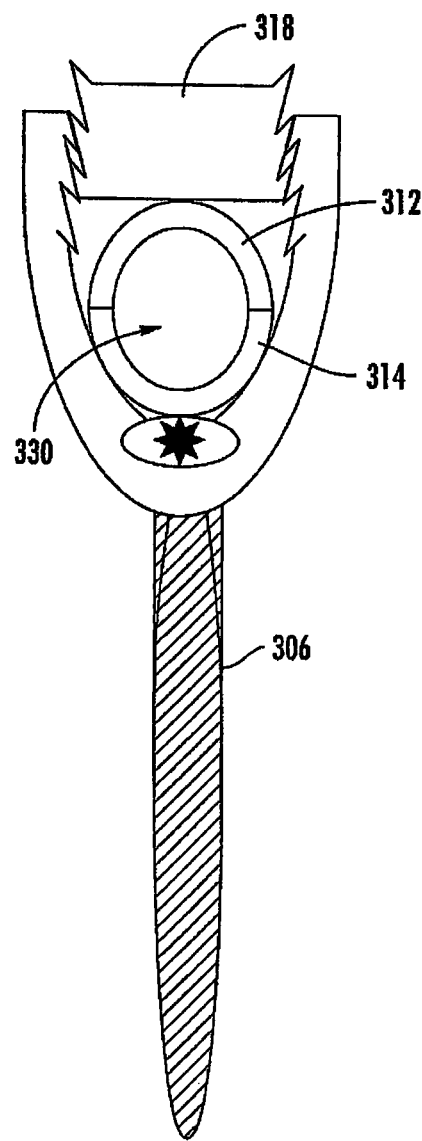
Figure 17A:
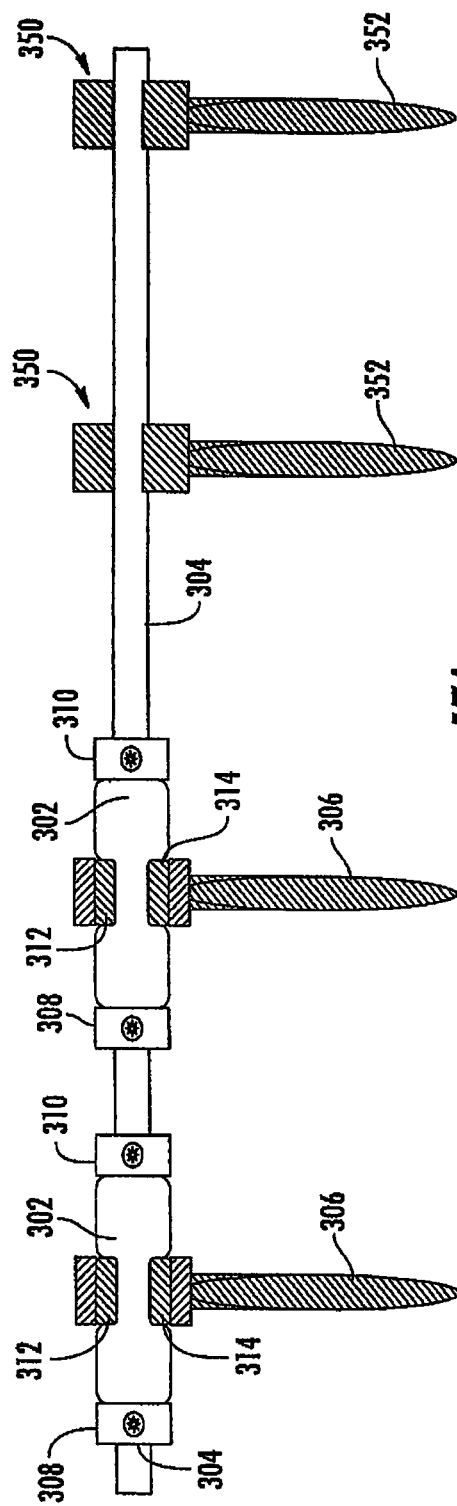
FIGS. 17A, 17B, 18A and 18B show integration of dynamic stabilization devices according to the disclosure with non-dynamic stabilization devices.
Figure 18A:
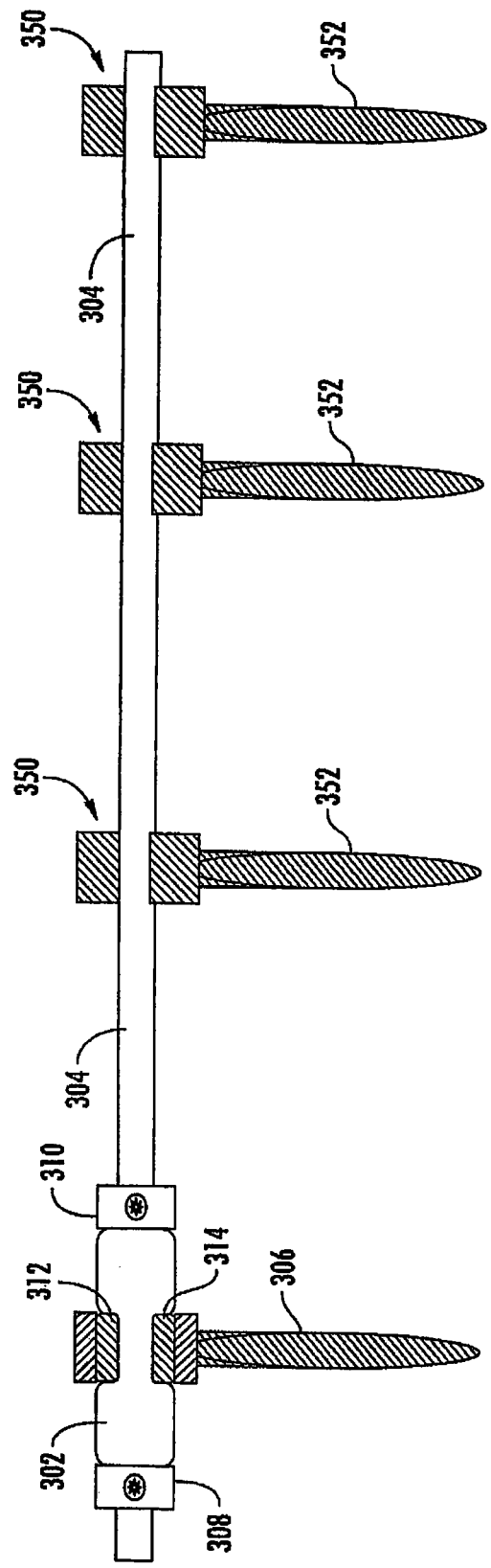
Figure 17B:
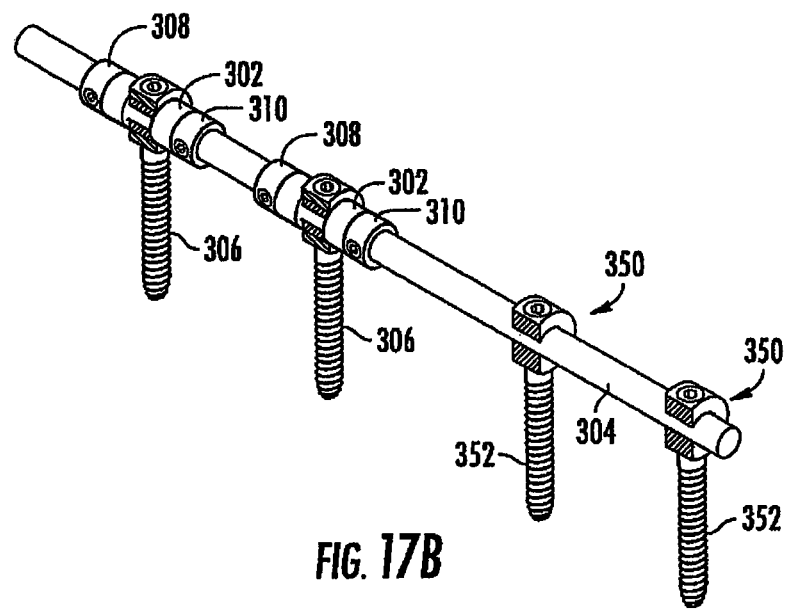
Figure 18B:
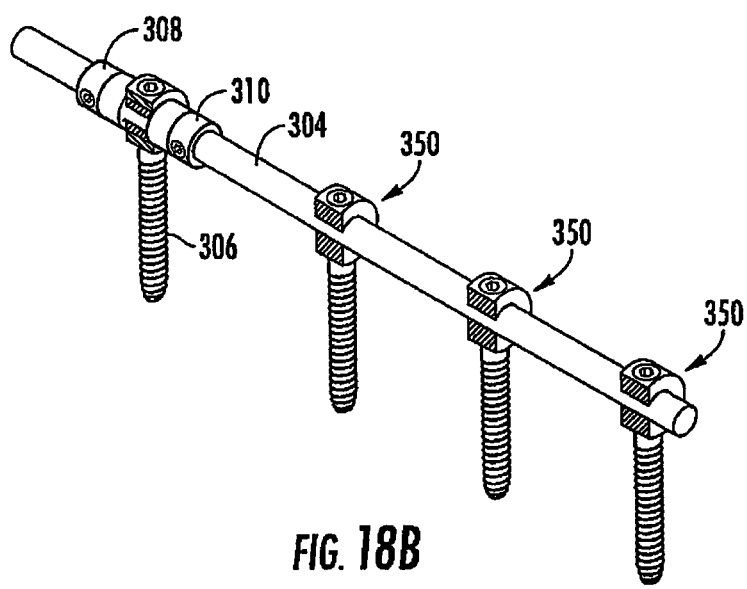

A pair of sleeves 312 and 314 are positioned within a polyaxial head 316 of the screw 306 to receive the elastomeric member 302, and a set screw 318 is threadably received in by a threaded bore 320 of the head 316 to bear the sleeve 312 against the member 302. The threads of the screw 318 and the bore 320 are preferably oppositely angled relative to one another as shown in FIG. 16A to avoid splaying of the head 316. The system 300 as shown in FIGS. 13A-13C preferably includes a pair of the members 302 installed on the rod 304 on a pair of the screws 306 spaced apart from one another.

The sleeves 312 and 314 are shown as semi-cylindrical sleeves, however, it will be understood that they may be of various joining configurations capable of joining together, locking together, or otherwise interdigitating to fit together to capture the member 302.

Figure 14:
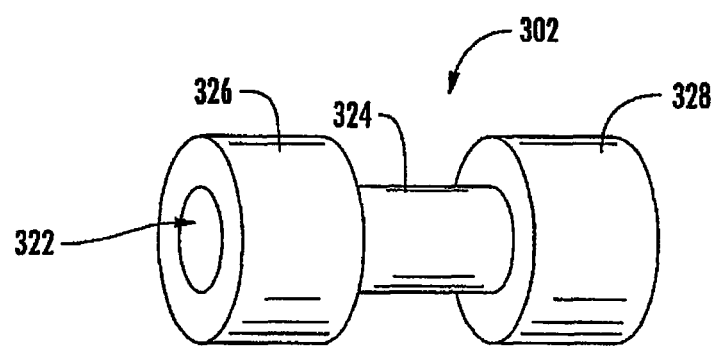
FIG. 14 shows a dumbbell shaped dampener of the system of FIGS. 13A-13C.
Figure 15:
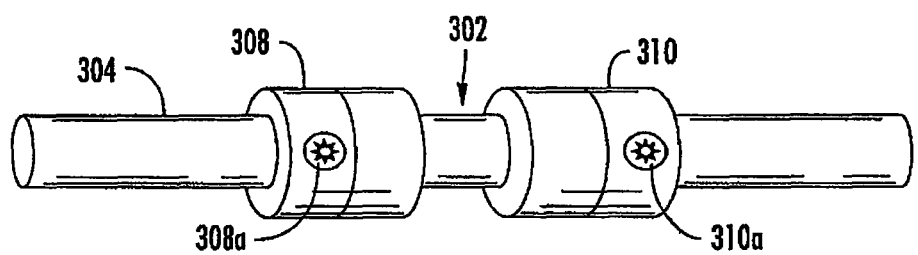
FIG. 15 shows the dampener installed on a support rod.

As shown in FIG. 14, the elastomeric member 302 is dumbbell shaped, having a through bore 322 sized to closely receive the rod 304. To provide the dumbbell shape, the member 302 includes a central cylindrical portion 324 of reduced outer diameter, and a pair of opposite cylindrical end portions 326 and 328 having enlarged outer diameters. As shown in FIG. 13B and FIG. 15, the rigid members 308 and 310 are installed on the rod 304 abutting ends of the member 302, when the spine is in a neutral condition.

As seen in FIGS. 13A-13C and FIGS. 16A and 16B, the sleeves 312 and 314 are positioned within the polyaxial head 316 of the screw 306 so as to fit together when urged by the set screw 318 to form a cylinder 330 sized to receive the central portion 324 of the elastomeric member 302. To accomplish this, the sleeve 312 is preferably pivotally secured to a lower surface of the set screw 318, such as by use of a pin that enables the sleeve 312 to swivel. The sleeves 312 and 314 are made of a rigid material, preferably metal corresponding to the metal of the screw 306. The set screw 318 and the shape of the head 316 capture the sleeves 312 and 314 such that there is no relative movement therebetween. However, the sleeves 312 and 314 serve to isolate the rod 304 from the metal screw 306, such that metal-to-metal contact is avoided when the rod 304 moves relative to the screw 306, and hence the sleeves 312 and 314.

Returning to FIGS. 13A-13C, the system 300 having a pair of the members 302 installed on the rod 304 on a pair of the screws 306 spaced apart from one another, is shown enabling improvement in spinal movements throughout the substantially normal range of motions from the neutral condition (FIG. 13B), to a flexion condition (FIG. 13A) and an extension condition (FIG. 13C).

As shown in FIG. 13B, the screws 306 are initially a distance X apart. This corresponds to the spine onto which the system 300 is installed being in the neutral condition, with the screws 306 installed in adjacent vertebrae. As will be observed, the elastomeric members 302 substantially fill the space between the rigid members 308 and 310 associated with each of the screws. Further, if desired, an elastomeric sleeve, such as one of the sleeves 52 may be provided in any remaining gaps, such as gap C.

In addition, it will be observed that metal-to-metal contact between metal components that are movable relative to one another is eliminated by the system 300. That is, the rod 304 and the screws 306 are each preferably made of metal, and the rod 304 has movement relative to the screws 306, as is apparent from comparison of the relative positioning of the screws and the rod in FIGS. 13A-13C.

For example, in the event the screws 306 move apart a distance Δx, such as occurs during flexion of the spine (FIG. 13A), the elastomeric members 302 prevent any metal-to-metal contact sites during a transition from neutral to flexion conditions of the spine, or during a transition to extension conditions of the spine when the screws become located closer to one another by the distance Δx (FIG. 13B). The members 302 also compress in a controlled manner to control movement of the rod in a desired manner to enable desired dynamic stabilization of the spine.

Thus, as will be appreciated, the system 300 advantageously provides a dynamic stabilization system that avoids metal-to-metal contact of components that move relative to one another and minimizes undesirable gaps between components of the system.

The components of the system 300 may be advantageously integrated into a treatment system that provides both dynamic stabilization and fusion or non-dynamic stabilization. For example, with reference to FIGS. 17A, 17B, 18A, and 18B, the components of the system 300 may be combined with one or more non-dynamic systems 350 having a pedicle screw 352 fixedly connected to the rod 304, as by a set screw, such that the rod does not move relative to the pedicle screw. Accordingly, portions of the rod 304 associated with the components of the system 300 offer dynamic stabilization with the rod 304 being movable relative to the pedicle screw 306, while the portions of the rod 304 associated with the non-dynamic systems 350 do not enable movement of the rod 304 relative to the screw 352.

Figure 20:
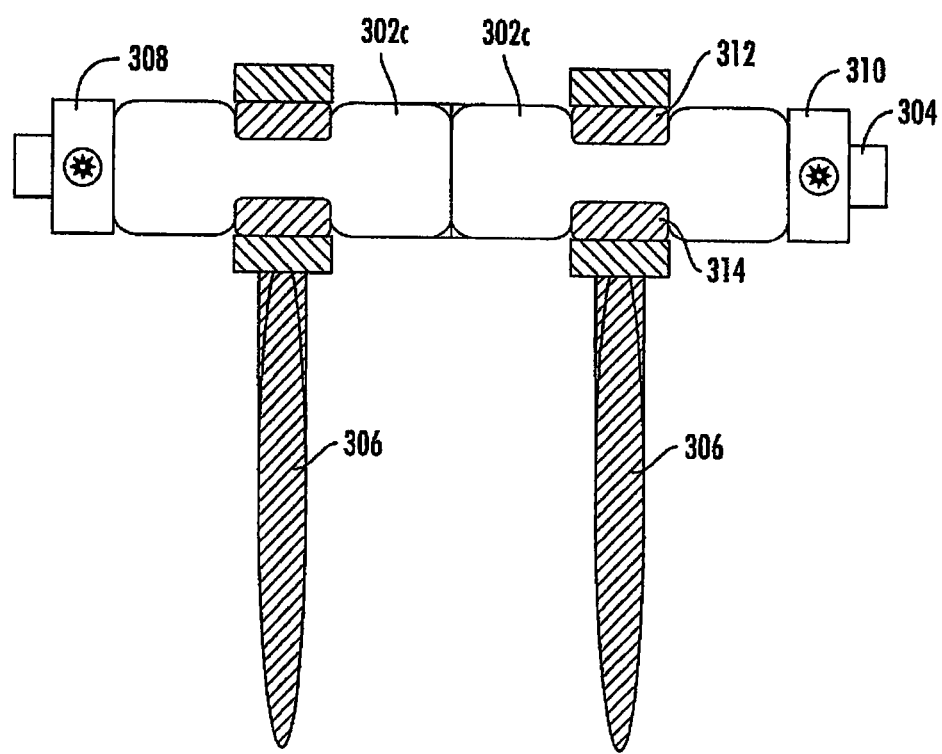
FIGS. 20 and 21 show alternate installations of the dampeners of FIGS. 19A-19C.
Figure 21:
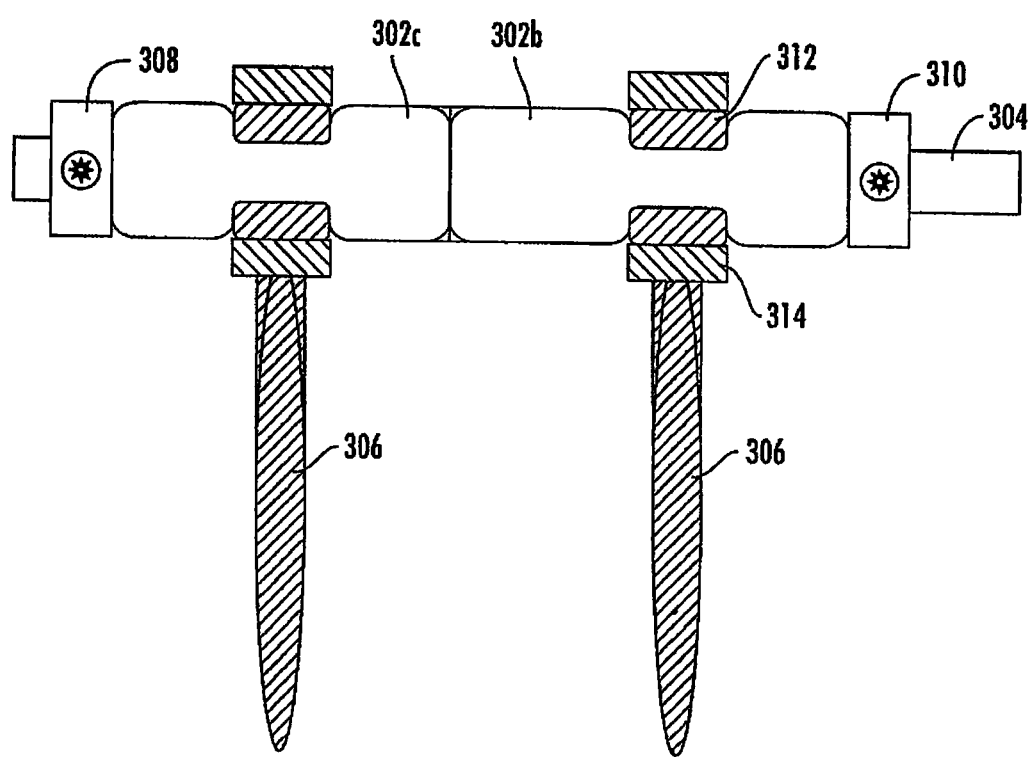

With reference to FIGS. 19A-19C, there are shown further embodiments of dumbbell shaped elastomeric members 302a-302c. The members 302a-302c are substantially identical to the member 302. However, the member 302a has an elongate end portion 360 that may be cut to fit during surgery to obviate the need for one or both of the rigid members 308 and 310. FIGS. 20 and 21 show installation of the members without intervening rigid members 308 and 310 between the elastomeric members. In this regard, the end portion 360 may be squared as shown and then rounded by cutting if desired. The squared ends may be desirably placed end-to-end as seen in FIGS. 20 and 21. The members 302b and 302c are identical to the member 302a, except they are made with the end portion 360 of various lengths so that thinning to length is not required. In this manner, an inventory of various dimensions of the members may be provided. This feature is especially important at the lumbosacral junction where the pedicle are often in close proximity.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A dynamic spinal stabilization system, comprising:
a metal support rod;

a dumbbell shaped elastomeric member having a through bore configured to receive the support rod and including a central portion of reduced outer dimension, and a pair of opposite end portions having enlarged outer dimensions;

a metal pedicle screw having a polyaxial head;

a set screw threadably received by the polyaxial head;

first and second rigid members securable to the rod; and a bottom partial sleeve positionable within a lower portion of the polyaxial head and a top partial sleeve positionable within an upper portion of the polyaxial head of the screw so as to mate with the bottom partial sleeve for receiving the central portion of the dumbbell shaped elastomeric member, wherein when the sleeves are installed within the polyaxial head the sleeves capture the central portion of the dumbbell with the opposite end portions of the elastomeric member extending outwardly from opposite sides of the polyaxial head, wherein the dumbbell shaped elastomeric member deforms to enable movement of the rod relative to the pedicle screw so as to permit spinal movements throughout a range of motions from a neutral condition of the spine, to a flexion condition, and an extension condition; and wherein the dumbbell shaped elastomeric member is operative to substantially eliminate contact between the metal rod and the metal pedicle screw so as to substantially eliminate metal-to-metal contact of the metal rod and the metal pedicle screw.

2. The system of claim 1, wherein the top partial sleeve is pivotally secured to a lower surface of the set screw.

3. The system of claim 1, further comprising a non-dynamic system comprising having a pedicle screw fixedly connected to the rod.

4. The system of claim 1, further comprising a plurality of dumbbell shaped elastomeric members.

5. The system of claim 1, wherein the dumbbell shaped elastomeric member is configured to be trimmed in a surgical procedure to provide a custom fit.

* * * * *